US006589568B2

United States Patent
Camper et al.

(10) Patent No.: US 6,589,568 B2
(45) Date of Patent: Jul. 8, 2003

(54) THERAPEUTIC BODY LOTION CONTAINING ALKALI METAL HYPOHALITE

(75) Inventors: Jurdon Wayne Camper, Rolla, ND (US); Marilyn A. Delorme, Bellcourt, ND (US); John E. Festvog, Rolla, ND (US)

(73) Assignee: Nurad, Inc., Urbandale, IA (US)

( * ) Notice: Subject to any disclaimer, the term of this patent is extended or adjusted under 35 U.S.C. 154(b) by 0 days.

(21) Appl. No.: 09/784,214

(22) Filed: Feb. 16, 2001

(65) Prior Publication Data

US 2002/0114849 A1 Aug. 22, 2002

(51) Int. Cl.⁷ .......................... A61K 33/14; A01N 59/00
(52) U.S. Cl. ....................... 424/661; 424/401
(58) Field of Search .............. 424/401, 78.02, 424/78.07, 661

(56) References Cited

U.S. PATENT DOCUMENTS

| | | | |
|---|---|---|---|
| 4,737,307 A | 4/1988 | Brown et al. ............... | 252/106 |
| 4,927,641 A | * 5/1990 | Knight ........................ | 424/665 |
| 5,273,678 A | 12/1993 | Deroux et al. ......... | 252/187.26 |
| 5,427,801 A | 6/1995 | Uehara ........................ | 424/616 |
| 5,472,715 A | 12/1995 | Uehara ........................ | 424/613 |
| 6,077,502 A | 6/2000 | Witt et al. .................... | 424/53 |

OTHER PUBLICATIONS

Davis, Logan J., "Good for what ails you", Turtle Mountain Times (Belcourt, N.D.), vol. 7, Issue 17 (Feb. 7, 2000).

* cited by examiner

*Primary Examiner*—Jose' G. Dees
*Assistant Examiner*—Konata M. George
(74) *Attorney, Agent, or Firm*—Brian J. Laurenzo; Michael C. Gilchrist; Jason M. Hunt

(57) ABSTRACT

A topically applied composition capable of treating subcutaneous tissue comprising an alkali metal hypohalite (AMH) (preferably, sodium hypochlorite) and a conventional skin lotion. The skin lotion serves both as a carrier and as an antidrying agent for the AMH. The AMH penetrates through the skin's pores and lymph nodes into the subcutaneous tissue. The AMH stimulates the immune system to alleviate, and sometimes cure, inflammation, aches, pains, and other symptoms caused by microbial (e.g., viral, bacterial, fungal and parasitic) infection, arthritis, hemorrhoids, allergies, etc.

13 Claims, No Drawings

THERAPEUTIC BODY LOTION CONTAINING ALKALI METAL HYPOHALITE

FIELD OF THE INVENTION

The instant invention is a topically applied therapeutic composition containing an alkali metal hypohalite (AMH). More particularly, the instant invention is a topically applied lotion that delivers AMH into the subcutaneous tissue and, thereby, stimulates the immune system to treat, and in some cases cure, a variety of ailments including: viral infections (e.g., colds, herpes, HIV infection, and shingles); microbial infections, Lyme disease, dermatitis; allergies; hemorrhoids; arthritis; and gout.

BACKGROUND ART

The most common AMH is sodium hypochlorite (NaOCl). Sodium hypochlorite is the active agent in household bleach and has been used as a bactericide since the beginning of the 19th century.

A number of compositions containing sodium hypochlorite have been patented. Representative patents include U.S. Pat. Nos. 4,737,307; 4,927,641; 5,273,678; 5,472,714; and 5,427,801.

U.S. Pat. No. 4,737,307 is directed to a skin cleanser capable of removing smegma and surface bacteria fungus and viruses from the surface of the skin. The cleanser is an aqueous solution of cetylpyridinium chloride, chlorine dioxide, sodium hypochlorite, polyoxyethylene (20) sorbitan monostearate and sodium benzoate.

U.S. Pat. No. 4,927,641 is directed to a veterinary liniment and method of employing the same. The liniment comprises dimethlysulfoxide and sodium hypochlorite. The liniment is preferably a thin liquid but may be in the form of a lotion, gel, or cream.

U.S. Pat. No. 5,273,678 is directed to a stable aqueous solution containing sodium hypochlorite, a pH regulator, and water. The solution is used as an antiseptic.

U.S. Pat. Nos. 5,472,715 and 5,427,801 are directed to an antifungal agent for the treatment of skin diseases, such as athlete's foot, ringworm and tinea, caused by dermatophytes, eczema, tinea or various fungi. The antifungal agent comprises a detergent solution of sodium hypochlorite, sodium sulfite, sodium nitrate, sodium chlorate, potassium chlorate, hydrogen peroxide, oxone water, sodium nitrite, potassium nitrite, nonionic surface active agent, and water.

With the exception of U.S. Pat. No. 4,927,641, these references are directed to compositions where any active ingredient appears to remain in the epidermal layer of the skin, i.e., the uppermost layer of the skin cells. None of these references recognize AMH's ability to stimulate the immune system and alleviate and/or cure the aches, pains, inflammation, itching, and other symptoms of many common maladies including viral infections (e.g., colds, herpes, HIV infection, and shingles), microbial infections, dermatitis, Lyme disease, allergies, hemorrhoids, arthritis and gout. Finally, the preferred topical system in all of these references is a solution—not a lotion.

There are a number of antimicrobial (e.g., antiviral, antibacterial, antifungal, antiparasitic) treatments on the market today for treating infections in subcutaneous tissue. In addition, there is a large body of art dedicated to treating internal ailments such as hemorrhoids, arthritis and allergies.

However, most of the treatments disclosed in the art deliver the active ingredient orally (i.e., in a pill, capsule or liquid form) or intravenously (i.e., by injection). These delivery methods, while effective, are problematic. Intravenous delivery can be difficult and is relatively costly. Oral delivery is often hampered by the foul taste of the active ingredient employed.

In addition, many of these treatments cause side effects. Common side effects include fatigue, raised blood pressure, skin irritation, and a weakened immune system.

SUMMARY OF THE INVENTION

The present invention is directed to a topically applied therapeutic composition. The composition comprises: (i) an alkali metal hypohalite (AMH); and (ii) a commercially available lotion. The final composition (hereinafter referred to as the "therapeutic lotion") is applied over the region of the body where symptoms, such as aches, sores, and inflamation, first arise.

The AMH is the active ingredient and is preferably sodium hypochlorite. The instant invention delivers AMH to the dermal, epidermal and, most importantly, to the subcutaneous tissue. Once in the body, the AMH stimulates the immune system to treat, and in some cases cure, a variety of ailments including viral and bacterial infections such as the common cold, herpes, Lyme disease, HIV infection and shingles; dermatitis; allergies; hemorrhoids; arthritis; gout; and elevated prostrate specific antigen.

The lotion component of the composition serves as both a carrier and anti-drying agent for the AMH. The lotion prevents the AMH from drying before it has enough time to penetrate through the skin pores and lymph nodes and down into the subcutaneous layers of tissue.

The invention does not cause common side effects, such as fatigue, raised blood pressure, or skin irritation. Nor does the invention adversely affect the user's immune system.

DETAILED DESCRIPTION OF THE INVENTION

The composition comprises, at the very least, an AMH and a conventional skin lotion. Other optional ingredients include common skin care aids and treatments such as Aloe Vera extract; petroleum jelly, mineral oil, vegetable oil, anti-inflammatory agents, and odor masking or emitting agents. Odor masking or emitting agents are especially desirable to mask the smell of the AMH.

Preferably, the AMH is the principal active ingredient in the composition. More preferably, the AMH is the only active agent.

The preferred AMH is sodium hypochlorite. Another suitable AMH is potassium hypochlorite.

The lotion component of the therapeutic lotion serves as the carrier, or vehicle, for the AMH. Lotions, in contrast to solutions, do not need to be rubbed into the skin in order to stay in place, even though it is preferable to do so. Preferably, the lotion is in the form of a semi-viscous or viscous ointment, such as a cream or gel. Higher viscosity increases residence time, i.e., the time in which the active ingredient is in contact with the proper location of the body. Preferably, the lotion is the principal carrier and, more preferably, the only carrier.

In addition, the lotion component of the therapeutic lotion serves as an antidrying agent. It allows the AMH component to remain sufficiently liquid, for a sufficient period of time, to penetrate the epidermal and dermal layers of the skin through skin's pores and lymph nodes. If lotion, or an equivalent antidrying agent, is not employed, the AMH drys up almost immediately after application (within seconds) and is not effective. In contrast, when an AMH, such as sodium hypochlorite, is combined and mixed with skin lotion, it can remain active in a penetrable liquid state for more than 30 minutes. Preferably the lotion is the principal anti-drying agent and, more preferably, the only anti-drying agent.

The identity of the lotion component is not especially critical. The majority of lotions currently on the market are acceptable. The only real requirement is that the lotion cannot contain highly basic materials such as ammonia since such compounds may react with the AMH component.

Preferred lotion components contain the healing plant Aloe Vera, or an extract from the same. One especially preferred skin lotion is marketed under the brand name ST. IVE'S THERAPY LOTION™ which contains water, mineral oil, glyceryl stearate SE, steric acid, cytyl alcohol, Aloe, petrolatum, magnesium aluminum silicate, iocopheryl acetate (Vitamin E), glycerin dimethicone, rosemary extract, matreciarin extract (chamoline), sage extract, white nettle extract, retinyl palmitato (Vitamin A), cholecalicferol (Vitamin D), vegetable oil, sodium lauryl sulfate, phenoxyethanol, methylparalein, propyparaben, titrosodium, EDTA, fragrance yellow 5, blue 1.

The amount of AMH in the therapeutic lotion varies with the specific ailment being treated. For most ailments, anywhere from 10 milliliters (circa 0.33 fluid ounces) to 120 milliliters (circa 4.0 fluid ounces) of a 7.25% by volume aqueous solution of AMH (e.g., sodium hypochlorite) is added to 532 milliliters (circa 18 fluid ounces) of lotion component. More preferably, a 7.25% by volume aqueous solution of AMH is added in an amount ranging from 30 milliliters (circa 1 fluid ounce) to 90 milliliters (circa 3 fluid ounces) to 532 milliliters of lotion component. Obviously, proportionally less AMH solution is needed when the AMH in the solution is in a concentration higher than 7.25% by volume and proportionally more solution is needed when the AMH in the solution is in a concentration less than 7.25% by volume. These figures roughly correspond to a concentration of pure AMH that makes up about 0.13% to about 1.33%, and preferably about 0.39% to about 1.04%, by volume, of the entire therapeutic lotion. However, lotions with a pure AMH concentration as high as about 6.33% by volume are both safe and effective.

An especially preferred therapeutic lotion composition is identified herein as "Number 4 formulation." This formulation contains 60 ml (circa 2 fluid ounces) of 7.25% by volume aqueous sodium hypochlorite solution and 532 ml (circa 18 fluid ounces) of ST. IVE'S THERAPY LOTION™ (whose ingredients have already been described).

The therapeutic lotion may be mixed with other ingredients, depending upon the ailment. For example, the therapeutic lotion may contain Vaseline and Preparation H—especially in treating ailments involving inflammation and itching, such as hemorrhoids. Furthermore, fragrants may be added to mask the smell of the AMH.

The AMH penetrates into the subcutaneous tissue through the skin pores and lymph nodes. The AMH treats, and sometimes cures, a number of ailments, including microbial (e.g., viral, bacterial, fungal and parasitic) infection, hemorrhoids, arthritis, allergies, etc . . . The AMH does not adversely affect the user's immune system or the healthy cells in the body. In fact, the AMH is believed to vitalize the user's immune system and, thereby, promote the healing process.

In practice, the user rubs the composition onto or about the affected area of the body. For example, in the treatment of colds and allergies, the composition is applied about the eyes and nose of the user. Due to the presence of the skin lotion, the AMH (e.g., sodium hypochlorite) remains in a liquid state for more than 20 minutes which is sufficient time for it to penetrate the pores and lymph nodes of the user. When the composition eventually drys out, the user can easily wash it off the surface of the skin. In most cases, multiple applications are needed. However, the number and frequency of applications needed will vary depending upon the severity and type of ailment treated. Generally, however, the treatment is applied at least once a day.

Treatment with the therapeutic lotion may be used in conjunction with other treatments. This is especially true when the other treatment is a high concentration therapeutic bath of sodium hypohalite and water. Such a bath is described in detail in a concurrently filed and copending patent application listing the same inventors.

The following examples illustrate, but do not limit, the invention by detailing a preferred embodiment and the efficacy of the same in treating a variety of ailments:

EXAMPLE 1

Hemorrhoids

A 58 year old man had a severe case of hemorrhoids. The man was treated with a combination of Number 4 formulation, Vaseline and Preparation H. As already stated, Number 4 formulation contains 60 ml (circa 2 fluid ounces) of 7.25% by volume aqueous sodium hypochlorite solution and 532 ml (circa 18 fluid ounces) of ST. IVE'S THERAPY LOTION™. The ST. IVE'S lotion contains water, mineral oil, glyceryl stearate SE, steric acid, cytyl alcohol, Aloe, petrolatum, magnesium aluminum silicate, iocopheryl acetate (Vitamin E), glycerin dimethicone, rosemary extract, matreciarin extract (chamoline), sage extract, white nettle extract, retinyl palmitato (Vitamin A), cholecalicferol (Vitamin D), vegetable oil, sodium lauryl sulfate, phenoxyethanol, methylparalein, propyparaben, titrosodium, EDTA, fragrance yellow 5, blue 1.

In this example, the Vaseline constitutes approximately 2%, by volume, of the total therapeutic lotion. The Preparation H makes up approximately 10%, by volume, of the therapeutic lotion. The remainder of the therapeutic lotion is Number 4 formulation.

After only one application, the patient's tissue softened and pain subsided. In addition, visual evidence of swelling was diminished.

Similarly, a 56 year old white male with hemorrhoids was treated with Number 4 formulation twice a day from May 28, 1998 through May 31, 1998. The patient experienced 90% relief from both pain and swelling.

EXAMPLE 2

Rheumatoid Arthritis

A 50 year old white male diagnosed with rheumatoid arthritis applied Number 4 formulation to affected areas twice a day. Twelve days later the patient had complete relief from both pain and stiffness.

Similarly, a 59 year old woman diagnosed with severe rheumatoid arthritis was treated. The woman was classified as 80% disabled. The Number 4 formulation was applied to her affected areas on a daily basis. Soon she experienced pain relief and diminished swelling.

EXAMPLE 3

Respiratory Ailment

A 47 year old man was diagnosed with an upper respiratory ailment. He applied the Number 4 formulation above the upper respiratory tract and lymph nodes. He saw almost immediate results. His bronchial tubes began to clear up.

EXAMPLE 4

Rhino Virus (Cold)

A 60 year old woman was diagnosed with Rhino Virus, i.e. the common cold. She applied Number 4 lotion around her sinuses. Relief was observed within 15 to 20 minutes after application. The cold symptoms were completely gone the next day.

Similarly, a 16 year old female exhibiting head cold symptoms applied Number 4 formulation to the outside of her nose and to the areas around her neck and chest. Her cold symptoms disappeared in fifteen minutes.

EXAMPLE 5

Elevated Prostrate Specific Antigen

The normal range for Prostrate Specific Antigen (PSA) is less than 4.0 ng/ml. A 57 year old white male with an elevated PSA level of 20.4 ng/ml began treatment with Number 4 formulation on Oct. 19, 1997. On Nov. 12, 1997 his PSA level was back to relatively normal levels, i.e., 4.6 ng/ml.

EXAMPLE 6

Dermatitis

A 52 year old Native American male suffered from dermatitis. The dermatitis covered 80% of his body. After three applications of the Number 4 formulation, his dermatitis appeared under control.

EXAMPLE 7

HIV

A 50 year old female was diagnosed positive for HIV virus nine years prior to treatment. She had a CD4 cell level of around 130. The patient soaked every other day for a period of two weeks in a bath solution of sodium hypochlorite and water (using 1 quart of 7.25%, by volume, sodium hypochlorite per 32 gallons of water).[1] Additionally, the patient applied the Number 4 formulation daily to the lymph nodes and around the olfactory nerves. Within a few months her CD4 count was over 600. Note that a normal CD4 count is between 401 and 1532.

[1] This high concentration sodium hypochlorite bath treatment is the subject of a concurrently filed and copending patent application to the same inventors.

EXAMPLE 8

Lyme Disease

A 67 year old female was treated for Lyme disease. The patient soaked every other day, for a total of four times, in the bath solution of sodium hypochlorite and water described in Example 7. In addition, the patient applied the Number 4 formulation every day for one month. The symptoms of Lyme disease are no longer apparent.

EXAMPLE 9

Amyotrophic Lateral Sclerosis (ALS—Lou Gehrig's Disease)

A 54 year old white male diagnosed with ALS was suffering from continual cramping. The patient was treated with 30 minute soaks, every other day for four days, in the bath solution of sodium hypochlorite and water described in Example 7. Additionally, the Number 4 formulation was applied to the patient every day for a week. After treatment, the cramping stopped completely.

EXAMPLE 10

Genital Herpes

A 28 year old male was diagnosed with genital herpes. The Number 4 formulation was applied three times per day over an extended period of time. In four days, the herpes appeared to be in remission. After eight months, no reoccurrence of the herpes was observed.

EXAMPLE 11

Shingles

An 81 year old female was diagnosed with a severe case of shingles. The Number 4 formulation was applied to her affected skin. Within 45 minutes, the pain associated with shingles had subsided. The lesions associated with shingles cleared in four days. Over an extended period of time there was no observable reoccurrence.

While the invention has been described with reference to exemplary embodiments thereof, those skilled in the art will be able to make various modifications to the described embodiments without departing from the true spirit and scope of the invention as defined in the following claims and their equivalents.

What is claimed is:

1. A method for alleviating and/or curing microbial infection in subcutaneous tissues comprising the following steps:
   (i) mixing an alkali metal hypohalite (AMH) and a lotion to form a composition, wherein the lotion is the principal carrier and anti-drying agent, and the AMH is the principal active agent;
   (ii) topically applying said composition to the region of the body manifesting symptoms; and
   (iii) maintaining contact for a duration of time sufficient to ensure that the alkali metal hypohalite penetrates into the subcutaneous tissue.

2. The method of claim 1, wherein the AMH is sodium hypochlorite.

3. A method for alleviating and/or treating the symptoms of arthritis and/or gout comprising the following steps:
   (i) mixing an alkali metal hypohalite (AMH) and a lotion to form a composition, wherein the lotion is the principal carrier and anti-drying agent:
   (ii) topically applying said composition to the region of the body manifesting symptoms; and
   (iii) maintaining contact for a duration of time sufficient to ensure that he alkali metal hypohalite penetrates into the subcutaneous tissue.

4. The method of claim 3, wherein the AMH is the principal active agent.

5. The method of claim 3, wherein the AMH is sodium hypochlorite.

6. A method for alleviating and/or treating the symptoms of hemorrhoids comprising the following steps:
   (i) mixing an alkali metal hypohalite (AMH) and a lotion to form a composition, wherein the lotion is the principal carrier and anti-drying agent:
   (ii) topically applying said composition to the region of the body manifesting symptoms; and (iii) maintaining contact for a duration of time sufficient to ensure that he alkali metal hypohalite penetrates into the subcutaneous tissue.

7. The method of claim 6, wherein the AMH is the principal active agent.

8. The method of claim 6, wherein the AMH is sodium hypochlorite.

9. A method for alleviating and/or treating the symptoms of allergies, including inflammation, pain, and itching of the affected area of the body, comprising the following steps:
   (i) mixing an alkali metal hypohalite (AMH) and a lotion to form a composition, wherein the lotion is the principal carrier and anti-drying agent:
   (ii) topically applying said composition to the region of the body manifesting symptoms; and
   (iii) maintaining contact for a duration of time sufficient to ensure that he alkali metal hypohalite penetrates into the subcutaneous tissue.

10. The method of claim 9, wherein the AMH is the principal active agent.

11. The method of claim 9, wherein the AMH is sodium hypochlorite.

12. A topically applied therapeutic composition comprising:
   (i) an alkali metal hypohalite (AMH) as the only active agent; and
   (ii) a lotion as the only carrier wherein the lotion also functions as the only anti-drying agent, wherein, upon application to the skin, the AMH penetrates into subcutaneous tissue.

13. The composition of claim 12, wherein the AMH is sodium hypochlorite.

* * * * *